US006872793B1

(12) United States Patent
Schlueter

(10) Patent No.: US 6,872,793 B1
(45) Date of Patent: Mar. 29, 2005

(54) OPHTHALMIC AND OTORHINOLARYNGOLOGICAL DEVICE MATERIALS

(75) Inventor: Douglas C. Schlueter, Azle, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/892,689

(22) Filed: Jul. 16, 2004

Related U.S. Application Data

(60) Provisional application No. 60/493,149, filed on Aug. 7, 2003.

(51) Int. Cl.$^7$ .............................................. C08F 118/16
(52) U.S. Cl. .................... 526/326; 526/306; 526/307.6; 526/307.7; 526/318.1; 526/318.43; 526/318.44; 526/324; 526/325; 526/328.5; 526/347.1; 351/159
(58) Field of Search ............................. 526/306, 307.6, 526/307.7, 318.1, 318.43, 318.44, 324, 325, 326, 328.5, 347.1; 351/159

(56) References Cited

U.S. PATENT DOCUMENTS

| | | | |
|---|---|---|---|
| 4,613,640 A | 9/1986 | Deisler et al. | 524/264 |
| 5,290,892 A | 3/1994 | Namdaran et al. | 526/259 |
| 5,331,073 A | 7/1994 | Weinschenk, III et al. | 526/264 |
| 5,470,932 A | 11/1995 | Jinkerson | 526/312 |
| 5,483,003 A * | 1/1996 | Siol et al. | 525/309 |
| 5,639,810 A | 6/1997 | Smith, III et al. | 524/269 |
| 5,693,095 A | 12/1997 | Freeman et al. | 623/6 |
| 5,708,094 A | 1/1998 | Lai et al. | 525/296 |
| 6,723,816 B2 * | 4/2004 | Salamone et al. | 528/32 |

FOREIGN PATENT DOCUMENTS

WO    WO 98/27447    6/1998

OTHER PUBLICATIONS

Abuelyaman et al. US 2003/0203011 A1 Oct. 30, 2003.*
Boonstra et al., "Role of Particulate Fillers in Elastomer Reinforcement: A Review," *Polymer*, vol. 20, pp. 691–704 (1979).

Gu et al., "Preparation of High Strength and Optically Transparent Silicone Rubber," *Eur. Polym J.*, vol. 34(11), pp. 1727–1733 (1998).

Hawker et al., "Living Free Radical Polymerization: A Unique Technique for the Preparation of Controlled Macromolecular Architectures," *Accounts of Chemical Research*, vol. 30(9), pp. 373–382 (1997).

Meckel et al., *Thermoplastic Polyurethane Elastomers in Thermoplastic Elastomers*, 2$^{nd}$ Ed. Holden, G. Legge, N.R.; Quirk, R; Schroeder, H. E. Eds., Hanser Publishers, New York, (1996) Chapter 2, "Thermoplastic Polyurethane Elastomers," pp. 16–45.

Muhlebach et al., Synthesis of Amphiphilic Block Copolymers by Atom Transfer Radical Polymerization (ATRP), *Macromolecules*, vol. 31, pp. 6046–6052 (1998).

Pinchuk et al., "A New Family of Thermoplastic Elastomers for Ultra–Long Term Implant Based Upon a Backbone of Alternating Quaternary and Secondary Carbons," 24$^{th}$*Annual Meeting of the Society for Biomaterials*, p., 173, Apr. 22–26, 1998.

Weiss et al., "Block copolymer ionomers: 1. Synthesis and physical properties of sulphonated poly(styrene–ethylene/butylene–styrene)," *Polymer*, vol. 32(10), pp. 1867–1874 (1991).

Weiss et al., "Block copolymer ionomers: thermoplastic elastomers possessing two distinct physical networks," *Polymer Communications*, vol. 31, pp. 220–223 (1990).

Yu et al., "Poly[poly(isobornyl methacrylate–co–methyl methacryate) (poly(IBMA–co–MMA))–b–polybutadiene–b–poly(IBMA–co–MMA)] Copolymers: Synthesis, Morphology, and Properties," *Macromolecules*, vol. 30(21), pp. 6536–6543 (1997).

* cited by examiner

*Primary Examiner*—Helen L. Pezzuto
(74) *Attorney, Agent, or Firm*—Patrick M. Ryan

(57) ABSTRACT

Disclosed are soft, high refractive index device materials having improved strength. The materials contain microphase-separated aliphatic and aromatic domains.

15 Claims, No Drawings

OPHTHALMIC AND OTORHINOLARYNGOLOGICAL DEVICE MATERIALS

This application claims priority to U.S. Provisional Application Ser. No. 60/493,149 filed Aug. 7, 2003.

FIELD OF THE INVENTION

This invention is directed to improved ophthalmic and otorhinolaryngological device materials. In particular, this invention relates to soft, high refractive index acrylic device materials that have improved strength.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than silicone materials.

U.S. Pat. No. 5,290,892 discloses high refractive index, acrylic materials suitable for use as an intraocular lens ("IOL") material. These acrylic materials contain, as principal components, two aryl acrylic monomers. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable, high refractive index ophthalmic lens materials containing at least about 90 wt. % of only two principal components: one aryl acrylic hydrophobic monomer and one hydrophilic monomer. The aryl acrylic hydrophobic monomer has the formula

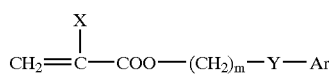

wherein:
X is H or $CH_3$;
m is 0–6;
Y is nothing, O, S, or NR, wherein R is H, $CH_3$, $C_nH_{2n+1}$ (n=1–10), iso-$OC_3H_7$, $C_6H_5$, or $CH_2C_6H_5$; and Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

The lens materials described in the '095 patent preferably have a glass-transition temperature ("$T_g$") between about −20 and +25° C.

Flexible intraocular lenses may be folded and inserted through a small incision. In general, a softer material may be deformed to a greater extent so that it can be inserted through an increasingly smaller incision. Soft acrylic or methacrylic materials typically do not have an appropriate combination of strength and flexibility to permit IOLs to be inserted through an incision as small as that required for silicone IOLs. The mechanical properties of silicone elastomers are improved by addition of an inorganic filler, typically surface treated silica. Surface treated silica improves the mechanical properties of soft acrylic rubbers, too, but reduces the optical clarity of the finished product. Alternative filler materials having a refractive index closer to soft acrylic rubber are needed.

The addition of reinforcing fillers to soft polymers is known to improve tensile strength and tear resistance. Reinforcement stiffens the polymer and improves its toughness by restricting the local freedom of movement of polymer chains, and strengthens the structure by introducing a network of weak fix points. The reinforcing ability of a particular filler depends upon its characteristics (e.g. size and surface chemistry), the type of elastomer with which it is used, and the amount of filler present. Conventional fillers include carbon black and silicate fillers, where the particle size (for maximum surface area) and wettability (for strength of cohesion) are of primary importance. Covalent chemical bonding between the matrix and the filler is generally not required for effective reinforcement. For a recent application and review see: Boonstra, "Role of particulate fillers in elastomer reinforcement: a review" *Polymer* 1979, 20, 691, and Gu, et al., "Preparation of high strength and optically transparent silicone rubber" *Eur. Polym. J.* 1998, 34, 1727.

U.S. Pat. No. 5,708,094 discloses polybutadiene-based compositions for contact lenses. The compositions are made from the polymerization product of a monomer mixture comprising polybutadiene compounds end-capped with a polymerizable ethylenically unsaturated group. These end-capped polybutadiene compounds are combined with conventional contact lens monomers.

SUMMARY OF THE INVENTION

Improved soft, foldable acrylic device materials which are particularly suited for use as IOLs, but which are also useful as other ophthalmic or otorhinolaryngological devices, such as contact lenses, keratoprostheses, corneal rings or inlays, otological ventilation tubes and nasal implants, have been discovered. These polymeric materials contain microphase-separated aliphatic and aromatic domains. The presence of the microphase-separated domains improves the strength and influences the surface properties of the polymeric materials.

DETAILED DESCRIPTION OF THE INVENTION

Unless indicated otherwise, all component amounts are presented on a % (w/w) basis ("wt. %").

The device materials of the present invention are self-reinforced polymeric materials. The materials can be made by the polymerization of a) an aromatic acrylate or methacrylate monomer (1) or styrenic monomer (2) with b) a difunctional macromonomer (3) having a number average molecular weight ($M_n$) of at least 3000 and a glass transition temperature ($T_g$) less than 0° C. The materials optionally contain a monofunctional macromonomer (4) having a $M_n$ of at least 1000.

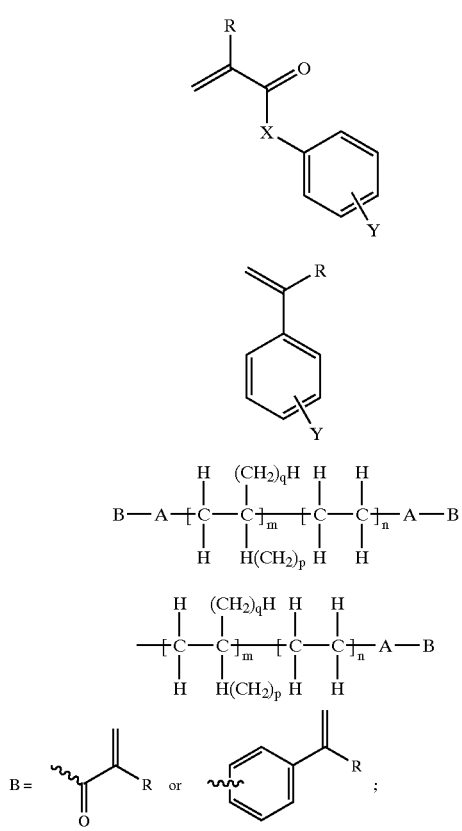

R=H, $CH_3$, $CH_2CH_3$;
X=$O(CH_2)_w$;
w=0–6;
Y=$(CH_2)_bH$, $O(CH_2)_bH$, H, Br, Cl, or F;
b=0–12;
p=0–22;
q=0–22;
A=O, NH, $OCH_2$, $OCH_2CH_2O$, $OC(O)NHCH_2CH_2O$; and m, n=co-monomer mole fraction where m<I and n=1−m.

Preferred monomers of formula (1) are those wherein R=$CH_3$; w=1–5 and Y=H. Preferred monomers of formula (2) are those wherein R=H and Y=H.

Preferred monomers of formulas (3) and (4) are those wherein A=O or $OC(O)NHCH_2CH_2O$; B=C(O)C(=$CH_2$)$CH_3$; p=2 and q=0, or p=q=1; and m=0.33–0.50.

Monomers of formulas (1) and (2) are known and can be made by known methods. See, for example, U.S. Pat. Nos. 5,331,073 and 5,290,892. Many monomers of formulas (1) and (2) are commercially available from a variety of sources.

Macromonomers of formulas (3) and (4) can be made by covalently attaching a polymerizable group to a functional end group of a saturated linear polyolefin. For example, polyisobutylene, ethylene-butylene copolymers or hydrogenated polybutadiene containing terminal hydroxyl groups are end-capped on one or both terminal chain ends with an acrylate, methacrylate or styrenic group. The end-caps are covalently attached via known methods, for example esterification with methacryloyl chloride or reaction with an isocyanate to form a carbamate linkage.

The copolymeric device material of the present invention contains from 20–70% of the monomer(s) of formula (1) or (2) and from 80–30% of the macromonomer of formula (3). The device material optionally contains one or more additional ingredients selected from the group consisting a monofunctional macromonomer of formula (4), a polymerizable UV absorber and a polymerizable colorant. If present, the monofunctional macromonomer of formula (4) is preferably present in an amount up to 80%, and most preferably 0.1–40%. Preferably, the device material of the present invention contains no other ingredients besides the monomers of formulas (1) and (2), the macromonomers (3) and (4), and polymerizable UV absorbers and colorants. For example, the device materials of the present invention do not contain a separate conventional cross-linking agent, such as ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; and their corresponding acrylates.

In order to form the device material of the present invention, the chosen ingredients are combined and polymerized using a radical initiator to initiate polymerization by the action of either heat or radiation.

Suitable polymerization initiators include thermal initiators and photoinitiators. Preferred thermal initiators include peroxy free-radical initiators, such as t-butyl (peroxy-2-ethyl)hexanoate and di-(tert-butylcyclohexyl) peroxydicarbonate (commercially available as Perkadox® 16 from Akzo Chemicals Inc., Chicago, Ill.). Particularly in cases where the materials of the present invention do not contain a blue-light absorbing chromophore, preferred photoinitiators include benzoylphosphine oxide initiators, such as 2,4,6-trimethyl-benzoyldiphenyl-phosphine oxide, commercially available as Lucirin® TPO from BASF Corporation (Charlotte, N.C.). Initiators are typically present in an amount of about 5% (weight) or less.

The device material of the present invention optionally contains reactive UV absorbers or reactive colorants. A preferred reactive UV absorber is 2-(2'-hydroxy-3'-methallyl-5'-methylphenyl)benzotriazole, commercially available as o-Methallyl Tinuvin P ("oMTP") from Polysciences, Inc., Warrington, Pa. UV absorbers are typically present in an amount from about 0.1–5% (weight). Suitable reactive blue-light absorbing compounds include those described in U.S. Pat. No. 5,470,932. Blue-light absorbers are typically present in an amount from about 0.01–0.5% (weight). When used to make IOLs, the device materials of the present invention preferably contain both a reactive UV absorber and a reactive colorant.

The particular combination of the ingredients described above and the identity and amount of any additional components are determined by the desired properties of the finished device material. In a preferred embodiment, the device materials of the present invention are used to make IOLs having an optic diameter of 5.5 or 6 mm that are designed to be compressed or stretched and inserted through surgical incision sizes of 2 mm or less.

The device material preferably has a refractive index in the dry state of at least about 1.47 as measured by an Abbe' refractometer at 589 nm (Na light source) and 25° C. Optics made from materials having a refractive index lower than 1.47 are necessarily thicker than optics of the same power which are made from materials having a higher refractive index. As such, IOL optics made from materials with comparable mechanical properties and a refractive index lower than about 1.47 generally require relatively larger incisions for IOL implantation.

The microphase-separated materials will exhibit two glass-transition temperatures ("$T_g$"). The continuous phase and non-continuous phase will each exhibit a $T_g$. The $T_g$ of the continuous phase will determine the material's flexibility properties, and folding and unfolding characteristics, and is preferably less than about ±25° C., and more preferably less than about −20° C. The $T_g$ of the non-continuous phase has a lesser impact on the materials' flexibility than that of the continuous phase. $T_g$ is measured by differential scanning calorimetry at 10° C./min., and is generally determined at the midpoint of the transition of the heat flux curve.

The device material preferably has an elongation of at least 200%, more preferably between 300 and 800%, and a Young's modulus of less than 6.0 Mpa, more preferably less than 5.0 MPa. These properties indicate that a lens made from such material generally will fold easily and will not crack, tear or split when it is folded. Tensile properties of polymer samples are determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at standard laboratory conditions of 23±2° C. and 50±5% relative humidity using an Instron Material Tester model 4400 with a 50 N load cell. The grip distance is 14 mm and a crosshead speed is 500 mm/minute and the sample is pulled to failure. The elongation (strain) is reported as a fraction of the displacement at failure to the original grip distance ("Elongation"). The modulus is calculated as the instantaneous slope of the stress-strain curve at 0% strain ("Young's modulus") and 100% strain ("100% modulus). Stress ("Stress") is calculated at the maximum load for the sample, typically the load when the sample breaks, assuming that the initial area remains constant. Tear resistance was measured on unnicked 90° C. angle specimens (Die C) according to ASTM 0624-91 "Standard Test Method for Tear Strength of Conventional Vulcanized Rubber and Thermoplastic Elastomers". The test specimens were 20 mm total length, 9.0 mm guage length and a thickness of 0.9 mm. Testing was performed on samples at standard laboratory conditions of 23±2° C. using an Instron Material Tester model 4400 with a 50 N load cell. The grip distance was 9.0 mm and the crosshead speed was 500 mm/minute and the sample was pulled to failure. The tear resistance ("Tear strength") was calculated from the maximum force obtained during testing divided by the sample thickness.

IOLs constructed of the device materials of the present invention can be of any design capable of being stretched or compressed into a small cross section that can fit through a 2-mm incision. For example, the IOLs can be of what is known as a one-piece or multi-piece design, and comprise optic and haptic components. The optic is that portion which serves as the lens and the haptics are attached to the optic and are like arms that hold the optic in its proper place in the eye. The optic and haptic(s) can be of the same or different material. A multi-piece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use as other ophthalmic or otorhinolaryngological devices such as contact lenses, keratoprostheses, corneal inlays or rings, otological ventilation tubes and nasal implants.

The invention will be further illustrated by the following examples, which are intended to be illustrative, but not limiting.

EXAMPLE 1

A glass vial was charged with 1.6731 g of difunctional macromer [5] having a number average molecular weight ($M_n$) of about 3400 and an ethylene/butylene molar ratio of about 2.2:1, 0.4519 g of styrene [6], and 0.0386 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure then closed and cured at 110° C. for 18.5 hr. The resulting material exhibited excellent clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile and thermal properties are listed in Tables 1 and 3.

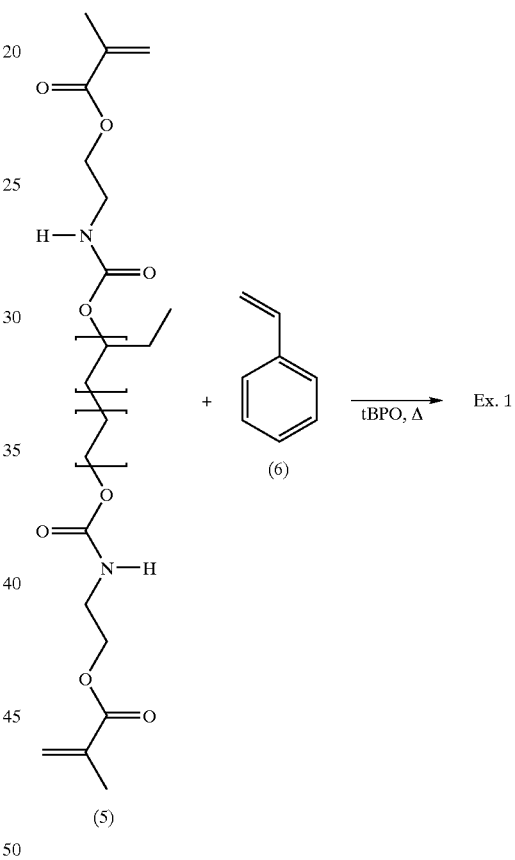

EXAMPLE 2

A glass vial was charged with 1.7056 g of the same difunctional macromer [5] used in Example 1, 0.6813 g of benzyl methacrylate (BzMA), and 0.0424 g of t-butyl peroxy-2-ethyl hexanoate (t-BPO). The monomer mixture was blended thoroughly and poured into a polypropylene mold. The open mold assembly was then placed under vacuum to remove entrapped air from the monomer mixture. The filled mold was returned to ambient pressure, then closed and cured for 1 hr at 70° C. then 2 hrs at 110° C. The resulting material exhibited excellent clarity and acceptable flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile properties are listed in Table 1.

EXAMPLE 3

A glass vial was charged with 1.6916 g of the same difunctional macromer [5] used in Example 1, 0.6812 g of 2-phenylethyl methacrylate (2-PEMA), and 0.0445 g of t-butyl peroxy-2-ethyl hexanoate (t-BPO). The monomer mixture was blended thoroughly and poured into a polypropylene mold. The open mold assembly was then placed under vacuum to remove entrapped air from the monomer mixture. The filled mold was returned to ambient pressure, then closed and cured for 1 hr at 70° C. then 2 hrs at 110° C. The resulting material exhibited excellent clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile properties are listed in Table 1.

EXAMPLE 4

A glass vial was charged with 1.7952 g of the same difunctional macromer [5] used in Example 1, 0.7545 g of 3-phenylpropyl methacrylate (3-PPMA), and 0.0438 g of t-butyl peroxy-2-ethyl hexanoate (t-BPO). The monomer mixture was blended thoroughly and poured into a polypropylene mold. The open mold assembly was then placed under vacuum to remove entrapped air from the monomer mixture. The filled mold was returned to ambient pressure, then closed and cured for 1 hr at 70° C. then 2 hrs at 110° C. The resulting material exhibited excellent clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile properties are listed in Table 1.

EXAMPLE 5

A glass vial was charged with 2.1456 g of the same difunctional macromer [5] used in Example 1, 0.8809 g of 4-phenylbutyl methacrylate (4-PBMA), and 0.0463 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure, then closed and cured for 1 hr at 70° C. then 2 hrs at 110° C. The resulting material exhibited excellent clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile properties are listed in Table 1.

EXAMPLE 6

A glass vial was charged with 2.2465 g of the same difunctional macromer [5] used in Example 1, 0.9138 g of 5-phenylpentyl methacrylate (5-PPMA), and 0.0504 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure, then closed and cured for 1 hr at 70° C. then 2 hrs at 110° C. The resulting material exhibited excellent clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile properties are listed in Table 1.

EXAMPLE 7

A glass vial was charged with 2.4039 g of the same difunctional macromer [5] used in Example 1, 0.4182 g of monofunctional macromer [7] having a number average molecular weight ($M_n$) of 4200 and an ethylene/butylene molar ratio of 2:1, 1.0140 g of 2-phenylethyl methacrylate (2-PEMA) [8], and 0.0710 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure, then closed and cured for 1 hr at 70° C. then 2 hrs at 110° C. The resulting material exhibited excellent clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile and thermal properties are listed in Table 2.

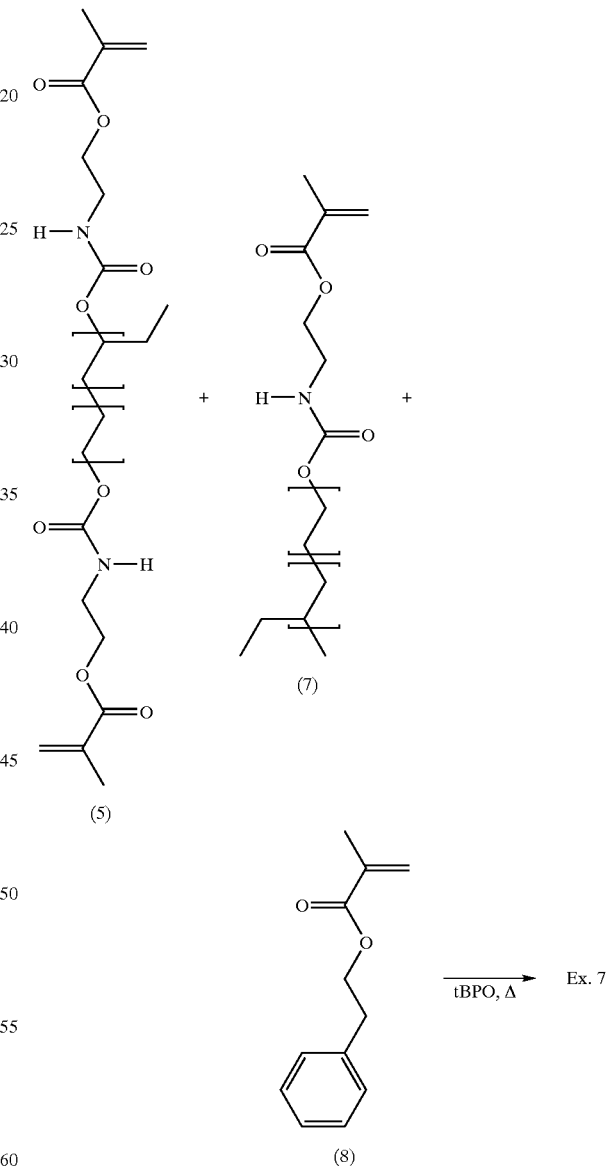

EXAMPLE 8

A glass vial was charged with 1.2705 g of the same difunctional macromer [5] used in Example 1, 1.2706 g of the same monofunctional macromer [7] used in Example 7, 0.8818 g of 2-phenylethyl methacrylate (2-PEMA), and 0.0640 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure, then closed and cured for 1 hr at 70° C. then 2 hrs at 110° C. The resulting material exhibited excellent clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile properties are listed in Table 2.

EXAMPLE 9

A glass vial was charged with 0.2008 of the same difunctional macromer [5] used in Example 1, 2.4000 g of the same monofunctional macromer [7] used in Example 7, 0.8667 g of 2-phenylethyl methacrylate (2-PEMA), and 0.0686 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure, then closed and cured for 1 hr at 70° C. then 2 hrs at 110° C. The resulting material exhibited excellent clarity and flexibility, and cured with minimal shrinkage. The cured polymer was extracted in refluxing acetone for 3 hrs.

The acetone was decanted and the product was rinsed with fresh acetone then dried under vacuum at 60° C. for 3 hrs. Representative tensile properties are listed in Table 2.

EXAMPLE 10

A glass vial was charged with 2.9598 g of difunctional macromer [5] having a number average molecular weight ($M_n$) of about 3400 and an ethylene/butylene molar ratio of about 2.2:1, 0.5749 g of styrene [6], and 0.0783 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure then closed and cured at 110° C. for 17.9 hr. The resulting material exhibited excellent clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile and thermal properties are listed in Table 3.

EXAMPLE 11

A glass vial was charged with 2.9179 g of difunctional macromer [5] having a number average molecular weight ($M_n$) of about 3400 and an ethylene/butylene molar ratio of about 2.2:1, 1.3259 g of styrene [6], and 0.0924 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure then closed and cured at 110° C. for 17.9 hr. The resulting material exhibited excellent clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile and thermal properties are listed in Table 3.

EXAMPLE 12

A glass vial was charged with 2.5226 g of difunctional macromer [5] having a number average molecular weight ($M_n$) of about 3400 and an ethylene/butylene molar ratio of about 2.2:1, 1.4144 g of styrene [6], and 0.0798 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure then closed and cured at 110° C. for 17.1 hr. The resulting material exhibited excellent clarity and acceptable flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile and thermal properties are listed in Table 3.

EXAMPLE 13

A glass vial was charged with 2.3026 g of difunctional macromer [5] having a number average molecular weight ($M_n$) of about 3400 and an ethylene/butylene molar ratio of about 2.2:1, 1.6158 g of styrene [6], and 0.0866 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure then closed and cured at 110° C. for 17.1 hr. The resulting material exhibited excellent clarity and limited flexibility in comparison to the materials of Examples 1–12, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile and thermal properties are listed in Table 3.

EXAMPLE 14

A glass vial was charged with 1.9912 g of difunctional macromer [5] having a number average molecular weight ($M_n$) of about 3400 and an ethylene/butylene molar ratio of about 2.2:1, 1.7096 g of styrene [6], and 0.0735 g of t-butyl peroxy-2-ethyl hexanoate (t-BPO). The monomer mixture was blended thoroughly and poured into a polypropylene mold. The open mold assembly was placed under vacuum to remove entrapped air from the monomer mixture. The filled mold was returned to ambient pressure then closed and cured at 110° C. for 17.1 hr. The resulting material exhibited adequate clarity and flexibility, and cured with minimal shrinkage. The cured polymer was extracted in refluxing acetone for 3 hrs. The acetone was decanted and the product was rinsed with fresh acetone then dried under vacuum at 60° C. for 3 hrs. Representative tensile and thermal properties are listed in Table 3.

TABLE 1

| Example | 1 | 2 | 3 | 4 | 5 | 6 |
|---|---|---|---|---|---|---|
| Monomer of formula [1] or [2] | styrene | BzMA | 2-PEMA | 3-PPMA | 4-PBMA | 5-PPMA |
| Monomer of formula [1] or [2] (wt. %) | 21.3 | 28.5 | 28.7 | 29.6 | 29.1 | 28.9 |

TABLE 1-continued

| Example | 1 | 2 | 3 | 4 | 5 | 6 |
|---|---|---|---|---|---|---|
| Difunctional macromer of formula [3]: Macromer [5] (wt. %) | 78.7 | 71.5 | 71.3 | 70.4 | 70.9 | 71.1 |
| t-BPO | 1.8 | 1.8 | 1.9 | 1.7 | 1.5 | 1.6 |
| Stress (MPa) | 2.972 | 5.443 | 3.725 | 2.090 | 1.678 | 1.625 |
| Elongation (%) | 403 | 279 | 313 | 301 | 278 | 266 |
| Young's modulus (MPa) | 1.419 | 5.356 | 2.848 | 1.297 | 1.036 | 1.026 |
| 100% modulus (MPa) | 1.019 | 2.887 | 1.913 | 0.840 | 0.685 | 0.708 |
| Tear strength (N/mm) | 3.497 | 5.594 | 4.143 | 2.244 | 1.506 | 1.510 |
| $T_g$ (° C.) | −53, 14 | −56, 40 | −56, 8 | −57, 3 | −55, −5 | −56, −9 |

BzMA: benzyl methacrylate
2-PEMA: 2-phenylethyl methacrylate
3-PPMA: 3-phenylpropyl methacrylate
4-PBMA: 4-phenylbutyl methacrylate
5-PPMA: 5-phenylpentyl methacrylate
t-BPO: t-butyl peroxy-2-ethyl hexanoate

TABLE 2

| Example | 7 | 8 | 9 |
|---|---|---|---|
| Monomer of formula [1] | 2-PEMA | 2-PEMA | 2-PEMA |
| Monomer of formula [1] (wt. %) | 26.4 | 25.8 | 25.0 |
| Difunctional macromer of formula [3]: Macromer [5] (wt. %) | 62.7 | 37.1 | 5.8 |
| Monofunctional macromer of formula [4]: Macromer [7] (wt. %) | 10.9 | 37.1 | 69.2 |
| t-BPO (wt. %) | 1.9 | 1.9 | 2.0 |
| Stress (MPa) | 3.995 | 3.557 | 1.433 |
| Elongation (%) | 323 | 433 | 523 |
| Young's modulus (MPa) | 2.877 | 1.646 | 0.452 |
| 100% modulus (MPa) | 1.924 | 1.189 | 0.368 |
| Tear strength (N/mm) | 4.548 | 3.839 | 1.484 |
| Refractive index (25° C.) | 1.480 | 1.480 | 1.479 |
| $T_g$ (° C.) | −58, 22 | −59, 26 | −59, 35 |

2-PEMA: 2-phenyethyl methacrylate
t-BPO: t-butyl peroxy-2-ethyl hexanoate

TABLE 3

| Example | 10 | 1 | 11 | 12 | 13 | 14 |
|---|---|---|---|---|---|---|
| styrene [6] (wt %) | 16.3 | 21.3 | 31.2 | 35.9 | 41.2 | 46.2 |
| difunctional macromer of formula [3]: Macromer [5] (wt %) | 83.7 | 78.7 | 68.8 | 64.1 | 58.8 | 53.8 |
| Stress (MPa) | 2.513 | 2.972 | 6.575 | 8.445 | 10.416 | 13.905 |
| Elongation (%) | 382 | 403 | 629 | 674 | 682 | 684 |
| Young's modulus (MPa) | 1.104 | 1.419 | 3.110 | 4.835 | 7.805 | 17.152 |
| 100% modulus (MPa) | 0.798 | 1.019 | 2.048 | 2.734 | 3.984 | 5.900 |
| Tear strength (N/mm) | 2.488 | 3.497 | 5.594 | 7.076 | 9.103 | 12.529 |
| Refractive index (25° C.) | 1.485 | 1.485 | 1.508 | 1.512 | 1.517 | 1.525 |
| $T_g$ (° C.) | −53, 4 | −54, 14 | −52, 27 | −51, 27 | −49, 30 | −50, 34 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A polymeric ophthalmic or otorhinolaryngological device material comprising
   a) a monomer selected from the group consisting of an aromatic acrylate or methacrylate monomer of formula (1) and a styrenic monomer of formula (2), and
   b) a difunctional macromonomer of formula (3) having a number average molecular weight ($M_n$) of at least 3000 and a glass transition temperature ($T_g$) less than 0° C.

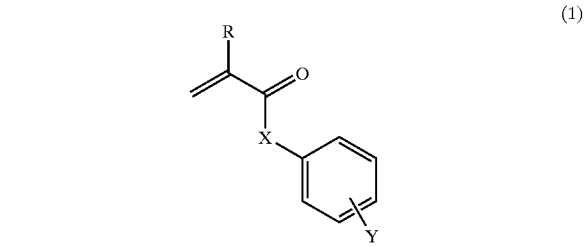

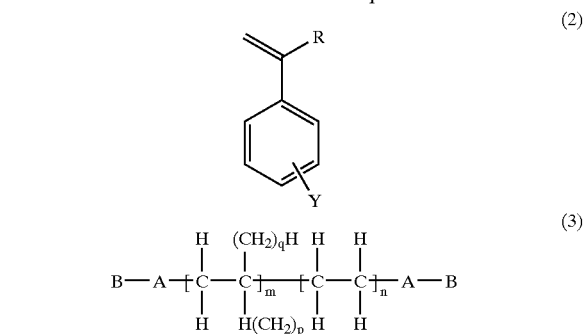

wherein

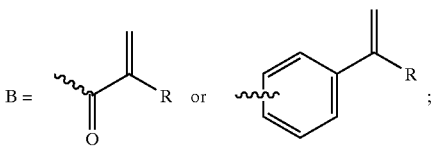

$R = H, CH_3, CH_2CH_3$;
$X = O(CH_2)_w$;
$w = 0-6$;
$Y = (CH_2)_bH, O(CH_2)_bH, H, Br, Cl,$ or $F$;
$b = 0-12$;
$p = 0-22$;
$q = 0-22$;
$A = O, NH, OCH_2, OCH_2CH_2O, OC(O)NHCH_2CH_2O$; and
m, n = co-monomer mole fraction where $m<1$ and $n=1-m$.

2. The device material of claim 1 wherein the device material further comprises a monofunctional macromonomer of formula (4) that has a number average molecular weight of at least 1000:

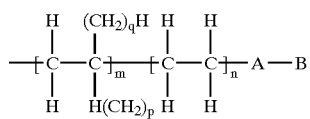

wherein

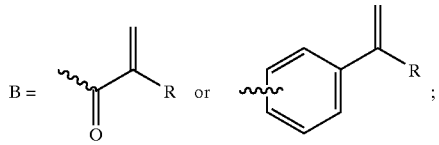

A=O, NH, OCH$_2$, OCH$_2$CH$_2$O, OC(O)NHCH$_2$CH$_2$O; and
p=0–22;
q=0–22; and
m, n=co-monomer mole fraction where m<1 and n=1−m.

3. The device material of claim 1 wherein in formula (1) R=CH$_3$; w=1–5 and Y=H; and in formula (2) R=H and Y=H.

4. The device material of claim 1 wherein in formula (3) A=O or OC(O)NHCH$_2$CH$_2$O; B=C(O)C(=CH$_2$)CH$_3$; p=2 and q=0, or p=q=1; and m=0.33–0.50.

5. The device material of claim 2 wherein in formula (4) A=0 or OC(O)NHCH$_2$CH$_2$O; B=C(O)C(=CH$_2$)CH$_3$; p=2 and q=0, or p=q=1; and m=0.33–0.50.

6. The device material of claim 1 wherein the device material comprises
 a) 20–70 wt. % of a monomer selected from the group consisting of an aromatic acrylate or methacrylate monomer of formula (1) and a styrenic monomer of formula (2), and
 b) from 80–30 wt. % of a difunctional macromonomer of formula (3).

7. The device material of claim 2 wherein the device material comprises up to 80 wt. % of the monofunctional macromonomer of formula (4).

8. The device material of claim 7 wherein the device material comprises 0.1–40 wt. % of the monofunctional macromonomer of formula (4).

9. The device material of claim 1 wherein the device material further comprises an ingredient selected from the group consisting of a polymerizable UV absorber and a polymerizable colorant.

10. The device material of claim 1 wherein the device material has a continuous phase T$_g$ of less than 25° C.

11. The device material of claim 10 wherein the device material has a continuous phase T$_g$ of less than −20° C.

12. The device material of claim 1 wherein the device material has an elongation between 300 and 800% and a Young's modulus of less than 6.0 MPa.

13. The device material of claim 12 wherein the device material has a Young's modulus of less than 5.0 MPa.

14. An ophthalmic or otorhinolaryngological device comprising the device material of claim 1.

15. The opthalmic or otorhinolaryngological device of claim 13 wherein the device is selected from the group consisting of intraocular lenses; contact lenses; keratoprostheses; corneal inlays; corneal rings; otological ventilation tubes; and nasal implants.

* * * * *